United States Patent
Fujita et al.

(10) Patent No.: US 7,532,964 B2
(45) Date of Patent: May 12, 2009

(54) DRIVER SEAT SYSTEM AND AWAKENING DEVICE

(75) Inventors: Etsunori Fujita, Hiroshima (JP); Yumi Ogura, Hiroshima (JP); Naoki Ochiai, Hiroshima (JP); Yasunori Noto, Fukuoka (JP); Tiejun Miao, Fukuoka (JP); Toshiyuki Shimizu, Fukuoka (JP)

(73) Assignee: Delta Tooling Co., Ltd., Hiroshima (JP)

( * ) Notice: Subject to any disclaimer, the term of this patent is extended or adjusted under 35 U.S.C. 154(b) by 897 days.

(21) Appl. No.: 10/849,769

(22) Filed: May 20, 2004

(65) Prior Publication Data
US 2004/0260440 A1    Dec. 23, 2004

(51) Int. Cl.
G06F 7/00        (2006.01)
(52) U.S. Cl. ................. 701/36; 701/49; 340/575; 340/576; 600/300; 600/485; 600/500; 600/504; 600/534; 600/529
(58) Field of Classification Search ............. 701/36, 701/49; 340/575, 576; 600/534, 300, 485, 600/500, 504, 529
See application file for complete search history.

(56) References Cited

U.S. PATENT DOCUMENTS

| | | | | |
|---|---|---|---|---|
| 4,706,072 A * | 11/1987 | Ikeyama | ................. | 340/576 |
| 5,127,708 A * | 7/1992 | Kishi et al. | ................. | 297/284.1 |
| 5,523,664 A * | 6/1996 | Ogasawara | ................. | 318/590 |
| 5,846,206 A * | 12/1998 | Bader | ................. | 600/534 |
| 6,014,081 A * | 1/2000 | Kojima et al. | ................. | 340/576 |
| 6,104,293 A * | 8/2000 | Rossi | ................. | 340/573.1 |
| 6,297,728 B1 * | 10/2001 | Rippbauer | ................. | 340/576 |
| 7,113,100 B2 * | 9/2006 | Yoshinori et al. | ................. | 340/575 |
| 7,277,758 B2 * | 10/2007 | DiLorenzo | ................. | 607/45 |
| 2002/0089425 A1 * | 7/2002 | Kubo et al. | ................. | 340/573.1 |
| 2004/0201481 A1 * | 10/2004 | Yoshinori et al. | ................. | 340/575 |
| 2006/0232430 A1 * | 10/2006 | Takaoka et al. | ................. | 340/575 |
| 2006/0235315 A1 * | 10/2006 | Akselrod et al. | ................. | 600/509 |
| 2007/0005609 A1 * | 1/2007 | Breed | ................. | 707/10 |
| 2007/0021915 A1 * | 1/2007 | Breed et al. | ................. | 701/301 |

* cited by examiner

*Primary Examiner*—Khoi Tran
*Assistant Examiner*—Jorge O Peche
(74) *Attorney, Agent, or Firm*—WolfBlock LLP

(57) ABSTRACT

There are provided a monitor for monitoring a human condition of a driver, and an awakening device for awakening a driver, which starts operation when received a predictive signal for fall-asleep being a signal for energy metabolism transition from an active state into a sleep state. The awakening device is structured to stimulate a pressure sense of the driver by reclining a seat back of a driver seat forward or rearward to thereby cause a shift force. Accordingly, without regard to an alarm reaction level to an alarm sound, it is possible to stimulate the driver and whereby awaken the driver more surely.

17 Claims, 11 Drawing Sheets

F I G. 8
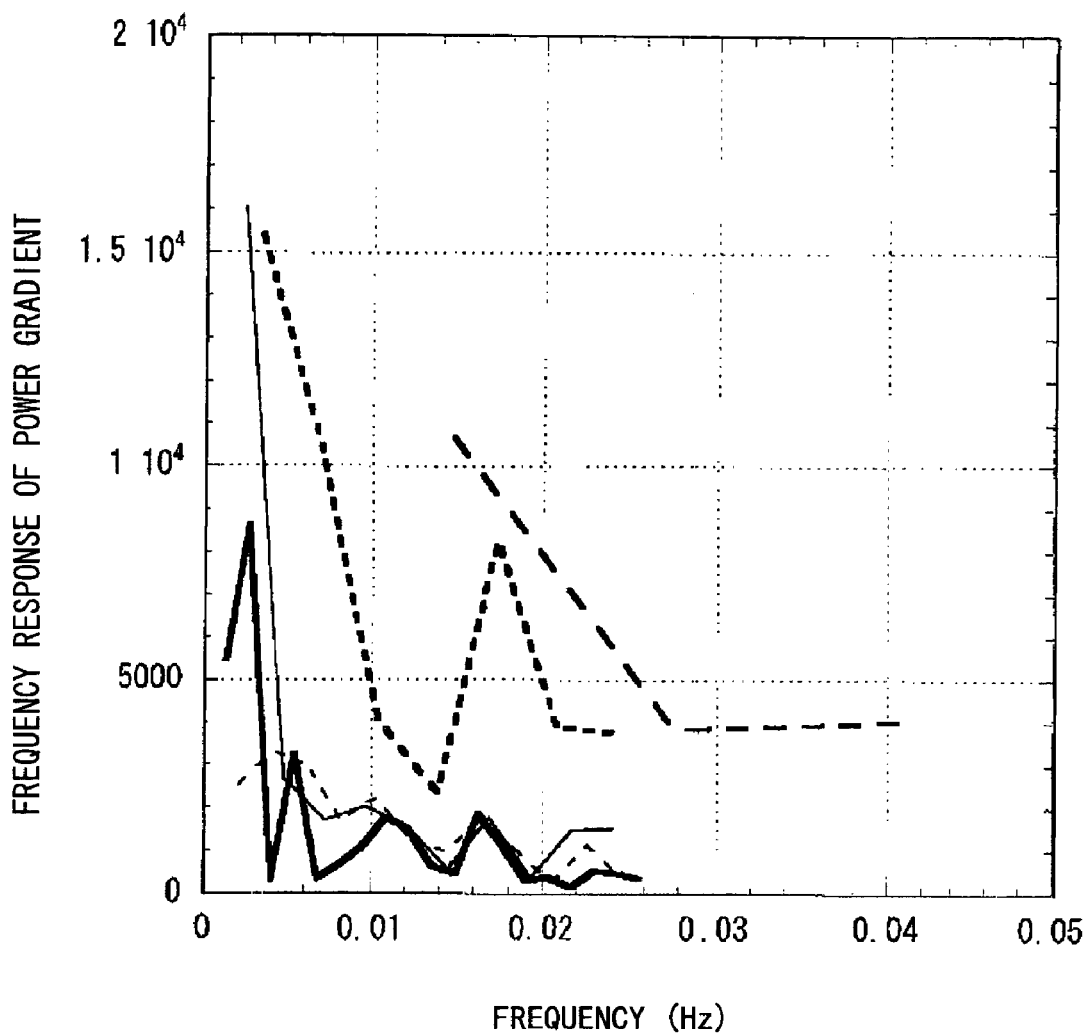

FIG. 10
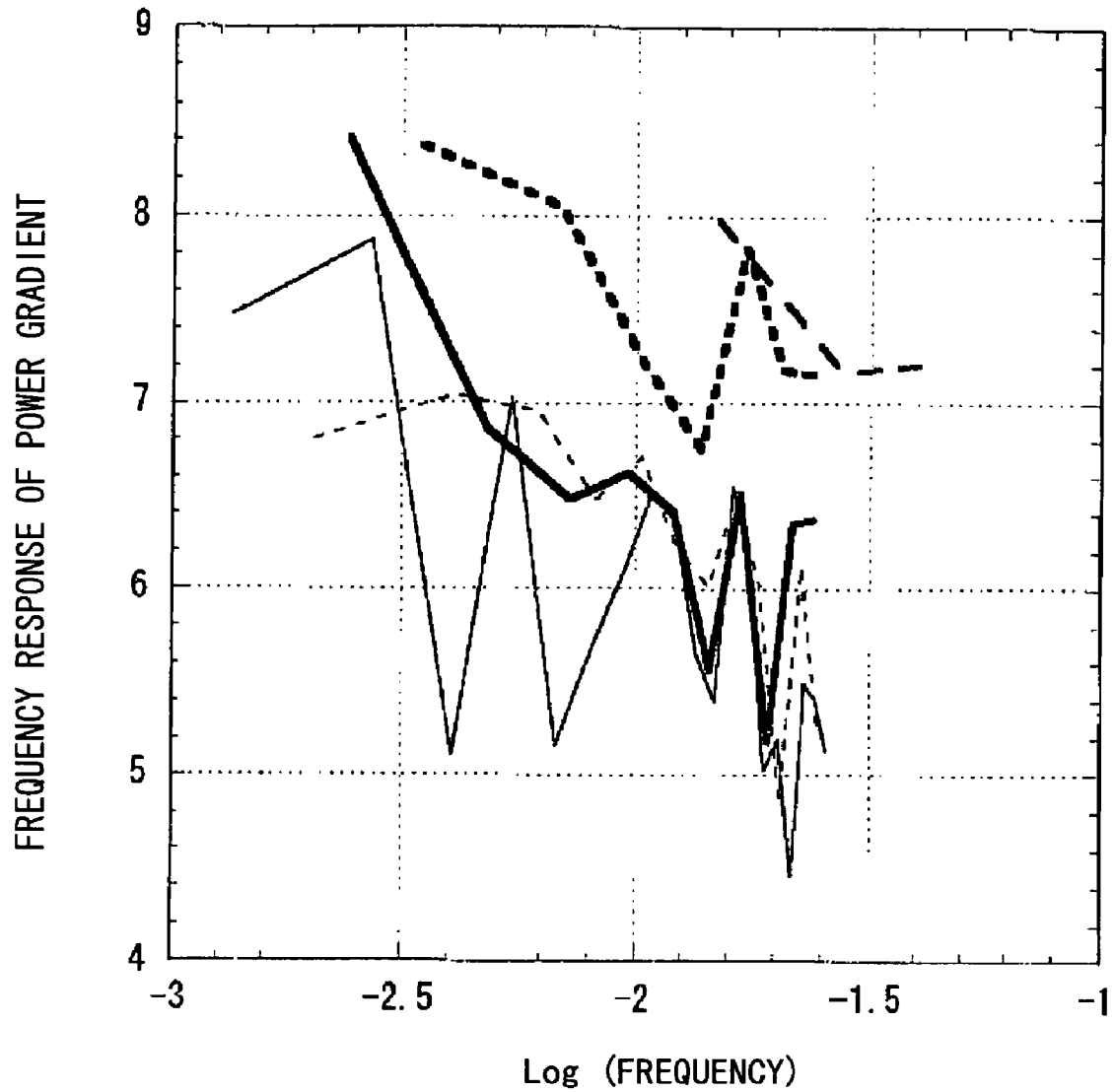
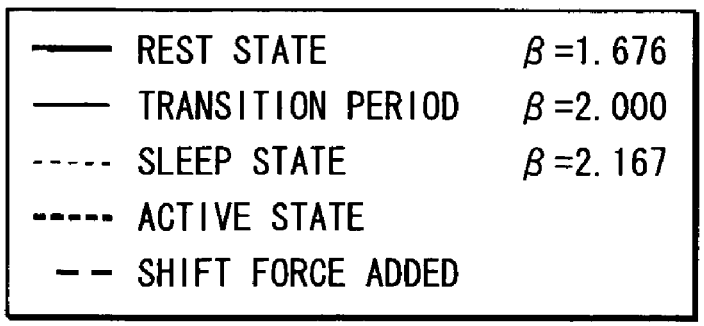

DRIVER SEAT SYSTEM AND AWAKENING DEVICE

FIELD OF INVENTION

The present invention relates to a driver seat system and an awakening device, and more particularly, to the driver seat system and the awakening device suitable for preventing a falling asleep at the wheel by detecting a predictive signal for falling asleep the signal being when the driver's energy metabolism makes transition from an active state to a sleep state to thereby awaken the driver before falling asleep.

BACKGROUND OF THE INVENTION

For detecting a condition of a human, for instance, he/she is either in the active state (wakeful state or awakening state) or in the sleep state, conventionally, a brain wave measurement and a pattern analysis on the brain wave are conducted. However, the brain wave measurement has to be conducted under conditions limiting a person's normal movement, for instance, a brain wave electrode and/or an eletrooculographic electrode is/are required to be set on a head of a subject, and so forth. Therefore, when operating a vehicle such as an automobile, a train, and the like, it is difficult to evaluate the human condition without imposing a strain on the subject.

Meanwhile, as a traffic accident prevention measure, a monitoring of the human condition (psychosomatic condition) of a driver in operation is receiving attention in recent years. For instance, techniques for monitoring the human condition using a heart beat or a pulse are proposed in patent document 1 (Japanese Patent Application Laid-Open No. Hei 9-308614) and patent document 2 (Japanese Patent Application Laid-Open No. Hei 10-146321). According to the techniques disclosed in patent documents 1 and 2, no setting of large-scale equipment is required for measuring brain wave, whereby facilitating the evaluation of the human condition of the driver.

The devices disclosed in patent documents 1 and 2 both determine a psychosomatic condition of the driver using a chaos indicator calculated from the heart beat or the pulse. Specifically, they are structured to calculate a Lyapunov exponent from the time-series data of the heart beat or the pulse, as one chaos indicator, and when the Lyapunov exponent shows, in its time-series change, a decline beyond a prescribed time, it is determined to be just before falling asleep (a state of feeling drowsy) due to a stress suffered at a level requiring a rest. It is already disclosed in Japanese Patent Application Laid-Open No. Hei 4-208136 that the chaos indicator of a bio-signal enables objective diagnosis of a human condition. It is therefore presumable that the devices disclosed in patent documents 1 and 2 are capable of detecting the state just before falling asleep.

However, in patent documents 1 and 2, as a concrete means for awakening the driver after detecting the state just before falling asleep, the disclosure is made only for making an alarm sound. The means for awakening the driver requires not to trouble the driver as much as possible, yet to awake the driver as surely as possible, whereas, certain people have weak response to the alarm sound, so that a development of a means capable of recovering the wakefulness even in such a case has been expected.

Moreover, in patent documents 1 and 2, the disclosure is made for the determination of a fatigue state of feeling drowsy only by the chaos indicator such as the Lyapunov exponent and the like, in which, in an attempt to determine the fatigue state of feeling drowsy, a process reaching a psychologically stabilized state is detected based on the declining change of the Lyapunov exponent, and in which the heat beat or the pulse measured is processed only for the chaos indicator.

Generally, a physical capability can be divided into that for survival, which is required for maintaining a life and that for activity, which is supported by the former. The physical capability for survival corresponds to a capability to maintain life and health, and is referred to as defensive physical capability, while the physical capability for activity is a behavioral physical capability for moving a body, and is generally understood as athletic ability. A function for supporting the physical capability for activity includes an energy generation system, an energy supply system, and an energy control system. The energy generation system functions for a muscular system measured by muscular strength, staying power, and the like, which causes a muscle fatigue. The energy supply system functions for a respiration and circulatory system measured by oxygen uptake and heart rate. The energy control system functions for alertness, cooperativeness, balance, and adoptability. Consequently, the functional status of the energy generation system causing muscle fatigue can be known by analyzing the state of the energy supply system or the energy control system.

Now, by obtaining the Lyapunov exponent of a bio-signal data, the state of the energy control system can be known, and by measuring a resistance force (power value) obtainable from a peak value for each cycle of the bio-signal, the state of the energy supply system can be known. Accordingly, with the use of the Lyapunov exponent or the power value, which are obtainable from the bio-signal data, the functional status of the energy generation system can be known. However, as mentioned before, currently, only the Lyapunov exponent is paid attention, and the power value is not within the scope for understanding the functional status of the energy generation system.

For more detail, as a characteristic of a fatigue state of feeling drowsy, the Lyapunov exponent sometimes shows a sharp downward trend, in other cases, a change in the power value can be seen sometimes more remarkable than the change in the Lyapunov exponent due to functional capability down of the energy supply system caused by energy release under the active state. Such a difference in change patterns largely depends on individual differences or health conditions. Therefore, for detecting an emergence of the fatigue state of feeling drowsy more properly, the time-series change in the Lyapunov exponent being an indicator of the state of the energy control system, and the time-series change in the power value being an indicator of the state of the energy supply system, are preferably used together in the system instead of using one.

In other words, the wakeful state or awakening state (active state) is a state psychologically stimulated and consuming higher calories, and when falling asleep, a person experiences a state psychologically relaxed but consuming still higher calories to reach to a state psychologically relaxed and consuming lower calories, or experiences a state psychologically stimulated but consuming lower calories to reach to the state psychologically relaxed and consuming lower calories. A typical sign indicating the former state psychologically relaxed but still consuming higher calories is an apparent decline in the Lyapunov exponent, and a typical sign indicating the latter state psychologically stimulated but consuming lower calories is an apparent decline in the power value. Based on this perspective, again, it is preferable to detect both the Lyapunov exponent and the power value instead of detecting one.

Further, in patent documents 1 and 2, the values of the Lyapunov exponent and the heart rate track the time-series changes thereof, while the value is detected for every 15 minutes or 30 minutes. Therefore, it is impossible to monitor the change in state substantially in real time, as required for a monitoring while driving.

OBJECTS AND SUMMARY OF THE INVENTION

The present invention is made in view of the above-described considerations, and an object of the present invention is to provide a driver seat system and an awakening device capable of awakening a driver as surely as possible when received a predictive signal for fall-asleep of the driver. Further, another object of the present invention is to provide the driver seat system suitable for preventing a falling asleep at the wheel more than ever by focusing attention on a time-series change in a power value in addition to a Lyapunov exponent of a bio-signal so that a determination of the predictive signal for fall-asleep from an active state to a sleep state can be made more accurately than ever.

More specifically, according to the present invention, a driver seat system composed of a monitor for monitoring a human condition of a driver, and an awakening device for making the driver recover a wakeful state or awakening state by starting operation when received a predictive signal for fall-asleep from the monitor, the predictive signal for fall-asleep being a signal when an energy metabolism makes transition from an active state into a sleep state, in which the awakening device includes a mechanism for stimulating a pressure sense (a sensation of pressure) of the driver, is provided.

According to the present invention, a driver seat system in which the awakening device for stimulating the pressure sense is a reclining mechanism for reclining a seat back of a driver seat forward or rearward to thereby stimulate the pressure sense of the driver by causing a shift force, is provided.

According to the present invention, a driver seat system in which an angle of the seat back of the driver seat to recline is set at an angle of 20 minutes to 5 degrees to the angle before reclining, is provided.

According to the present invention, a driver seat system in which the monitor includes a bio-signal measurement instrument for measuring a bio-signal of the driver, and a biosignal analyzer for analyzing a bio-signal data collected by the bio-signal measurement instrument, the bio-signal analyzer composed of:

a bio-signal peak value detection means for detecting a peak value for each cycle of an original waveform of the bio-signal data;

a power value calculation means for calculating a difference between the peak value at an upper limit side and the peak value at a lower limit side for each certain time range using respective peak values obtained by the bio-signal peak value detection means to thereby set the difference as a power value;

a gradient calculation means for obtaining a gradient of the power value with regard to time base in a certain time range by performing slide calculation the prescribed number of times at a prescribed overlap rate with regard to the prescribed time;

a comparative determination means for comparatively determining whether a sudden drop state of the gradient of the power value exists or not in time-series change in the gradient of the power value obtained by performing slide calculation with the gradient calculation means to thereby determine a time range in which the sudden drop state appears to be the predictive signal for fall-asleep from the active state into the sleep state; and an output means for outputting the predictive signal for fall-asleep from active state to the sleep state detected by the comparative determination means, is provided.

According to the present invention, a driver seat system in which the bio-signal analyzer further includes a Lyapunov exponent calculation means for calculating a Lyapunov exponent by performing chaos theory analysis on the bio-signal data, and a Lyapunov exponent peak value detection means for detecting a peak value for each cycle of a time-series change waveform of the Lyapunov exponent calculated by the Lyapunov exponent calculation means, in which the gradient calculation means includes a means for obtaining, in addition to the gradient of the power value, a gradient of respective peak values of the Lyapunov exponent with regard to time base in a certain time range obtained by the Lyapunov exponent peak value detection means, and in which the comparative determination means comparatively determines whether the sudden drop slate exists or not in at least one of the time-series changes in the gradients of the power value and the Lyapunov exponent obtained by performing slide calculation with the gradient calculation means to determine a range in which the sudden drop state appears to be the predictive signal for fall-asleep from the active state into the sleep state, is provided.

According to the present invention, a driver seat system in which the comparative determination means compares the time-series changes in the gradients of the power value and the Lyapunov exponent which are obtained by performing slide calculation with the gradient calculation means, and determines whether the gradient of the power value and the gradient of the Lyapunov exponent are in opposite phases with each other before or in the range the sudden drop appears in the gradient of the power value or in the gradient of the Lyapunov exponent, and in the case where the sudden drop in the gradient of the power value or in the gradient of the Lyapunov exponent appears while they are in the opposite phases, the comparative determination means determines the range to be the predictive signal for fall-asleep from the active state into the sleep state, is provided.

According to the present invention, a driver seat system in which the comparative determination means includes a means for determining that the transition into the sleep state is made when the time-series change in the gradient of the power value or in the gradient the Lyapunov exponent appear at a low amplitude on the whole after the sudden drop appears in the gradient of the power value or in the gradient of the Lyapunov exponent, respectively, is provided.

According to the present invention, a driver seat system in which the bio-signal peak value detection means includes a means for carrying out differentiation of the bio-signal data for smoothing to identify a range in the vicinity of a differential waveform gradient at zero degrees to thereby detect the peak value from the original waveform corresponding to the range identified, is provided.

According to the present invention, a driver seat system in which the Lyapunov exponent peak value detection means includes a means for carrying out differentiation of the Lyapunov exponent for smoothing and to identify a range in the vicinity of a differential waveform gradient at zero degrees to thereby detect the peak value from the original waveform corresponding to the range identified, is provided.

According to the present invention, a driver seat system in which the power value calculation means is a means for calculating, as a power value, a difference between an average peak value at the upper limit side and an average peak value at the lower limit side both in a certain time range of the bio-signal data, is provided.

According to the present invention, a driver seat system in which the gradient of the power value or the gradient of the Lyapunov exponent calculated by the gradient calculation means is a value obtained by a least-squares method, is provided.

According to the present invention, a driver seat system in which the bio-signal measurement instrument is a pressure sensor to be mounted in at least one of a seat cushion and the seat back of the driver seat, is provided.

According to the present invention, a driver seat system in which a cushioning layer composing the seat cushion and the seat back is a tension structure causing a difference in tension depending on presence or absence of a person seated on the driver seat, and in which the pressure sensor is mounted in the cushioning layer being the tension structure, is provided.

According to the present invention, a driver seat system further composed of a guide route search and display device for searching a guide route to a nearest parking area based on current location of a vehicle to display the guide route on a display of a vehicle navigation system when received the predictive signal for fall-asleep, the guide route search and display device being provided to be able to receive a signal from the monitor, is provided.

According to the present invention, a driver seat system further composed of a communication means capable of communicating the predictive signal for fall-asleep to a control center which controls, the communication means being provided to be able to receive a signal from the monitor, is provided.

According to an alternate embodiment of the present invention, an awakening device which starts operation when received a predictive signal for fall-asleep from an active state into a sleep state from a monitor for monitoring a human condition of a driver, composed of a mechanism for stimulating a pressure sense of the driver to awaken the driver, is provided.

According to the present invention, an awakening device in which the mechanism for stimulating the pressure sense is a reclining mechanism which simulates the pressure sense of the driver by causing a shift force by reclining a seat back of a driver seat forward or rearward, is provided.

According to the present invention, an awakening device in which an angle of the seat back of the driver seat to recline is set at an angle of 20 minutes to 5 degrees to the angle before reclining, is provided.

BRIEF DESCRIPTION OF THE DRAWINGS

The foregoing and still other objects and advantages of the present invention will be more apparent from the following detailed explanation of the preferred embodiments of the invention in connection with the accompanying drawings.

FIG. 8 is a graphical chart showing a result of a frequency analysis on the gradient of the power value in test example 4;

FIG. 10 is a graphical chart plotting a relation between frequency response of the gradient of the power value and frequency with regard to the logarithm axis based on the frequency analysis result in FIG. 8.

DETAILED DESCRIPTION OF THE INVENTION

Figure 1:
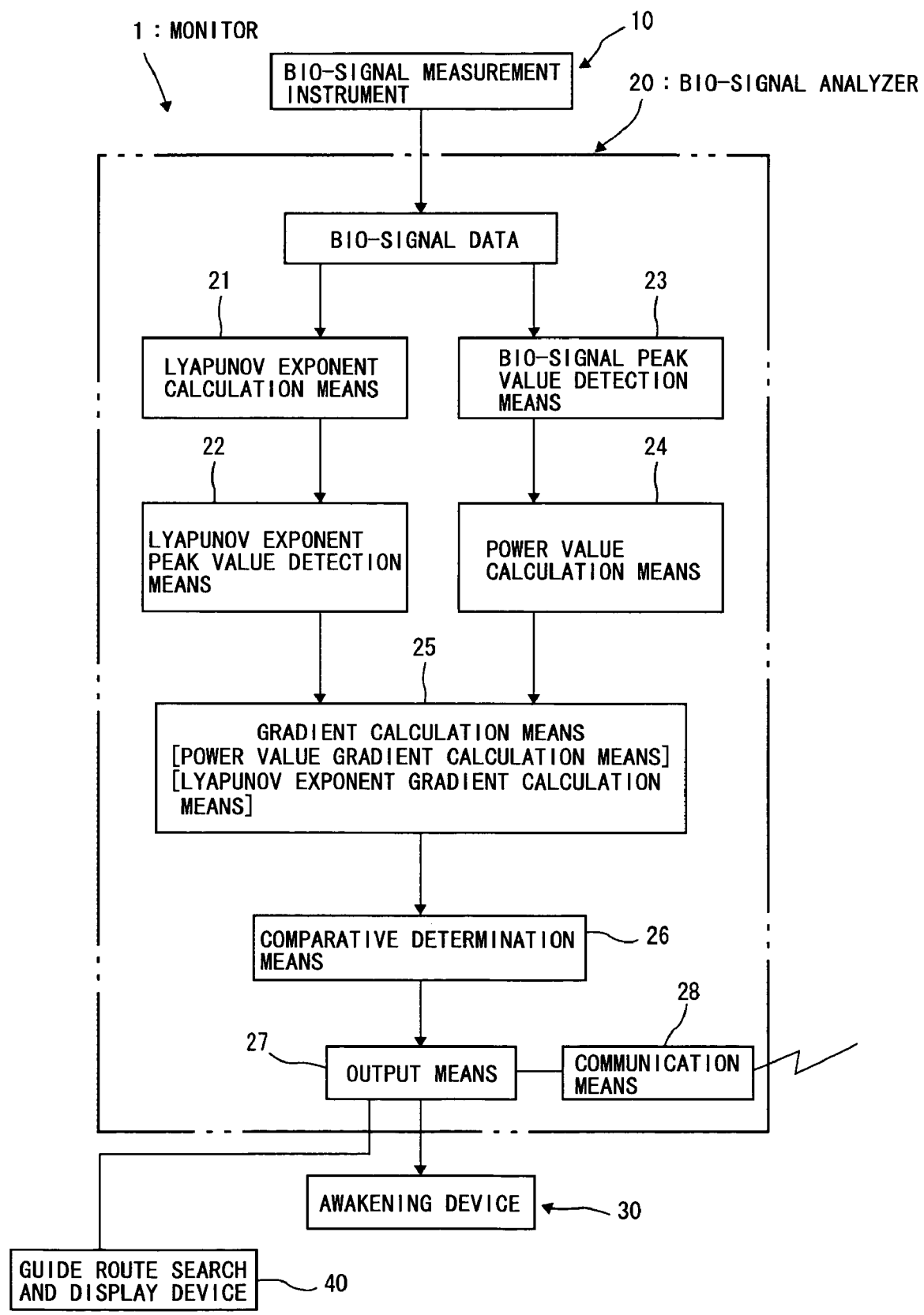
FIG. 1 is a block diagram showing a structure of a monitor according to an embodiment of the present invention.

Hereinafter, the present invention will be described in more detail based on embodiments shown in the drawings. FIG. 1 is a block diagram showing a monitor 1 used in a driver seat system according to an embodiment of the present invention. As shown in the drawing, the monitor 1 of the present embodiment is composed of a bio-signal analyzer 20 for receiving a bio-signal data detected by a bio-signal measurement instrument 10.

As a bio-signal measurement instrument 10, one provided with a sensor such as a pressure sensor can be used. For instance, the pressure sensor can be used by being mounted in at least one of a seat back and a seat cushion of a driver seat for a vehicle or a train. However, it is required not to give a person a feeling of something foreign when the person is seated thereon, whereby a film-shaped piezoelectric element is preferably used as a pressure sensor by being mounted in the seat back or the seat cushion. This makes it possible with ease to detect, as a fluctuation of a pressure value, a vibration of a body surface caused by a pulse-beat which is a bio-signal. The structure of the driver seat in which the bio-signal measurement instrument 10 is to be mounted is not limited, and thereby the bio-signal measurement instrument 10 is applicable to the driver seats of various types. For instance, it is also applicable to the driver seat, of which cushioning layer forming the seat back or the seat cushion is made of a polyurethane material.

However, as a cushioning layer for forming the seat back or the seat cushion, a tension structure is preferably used, the tension structure causing a difference in tension depending on presence or absence of a person seated on the seat. For instance, such a tension structure as spread over a frame member is preferably used. Additionally, such a cushioning layer may be made of such as a two-dimensional net member, the polyurethane material of a thin-type, or the like, whereas, a three-dimensional net member (solid knitted fabric), which is knitted by a Double Raschel knitting machine and the like with a connecting yarn shuttling between a pair of ground knitted fabrics placed at a predetermined interval, is preferably used. With the use of the solid knitted fabric as a tension structure, spring characteristics having a spring constant, which is close to that of a human muscle, can be easily provided. Therefore, subtle pressure fluctuations of muscles caused by a human respiration are transmitted to contacts of the seat cushion and the seat back, so that low-frequency vibrations in response to the respiration can be caused on the contacts. The low-frequency vibrations are fed back to the muscles thereafter and give the human body low-frequency pressures having an effect similar to low-frequency massages by external force. As a result, a seat capable of reducing postural off-balance, alleviating muscular contraction (tension), facilitating intravenous blood flow, keeping peripheral blood circulation in good condition, and whereby preventing fatigue is enabled.

It should be noted that the tension structure can be provided in any manner as long as it is provided to cause the difference in tension depending on presence or absence of the person seated on the seat, and the tension structure is not limited to the case where it is spread over the frame member. For instance, the case where wire members are disposed on the polyurethane foam in the width direction with a space therebetween and a cushioning member is provided as a tension structure by being spread over the wires, is also acceptable.

Figure 2:
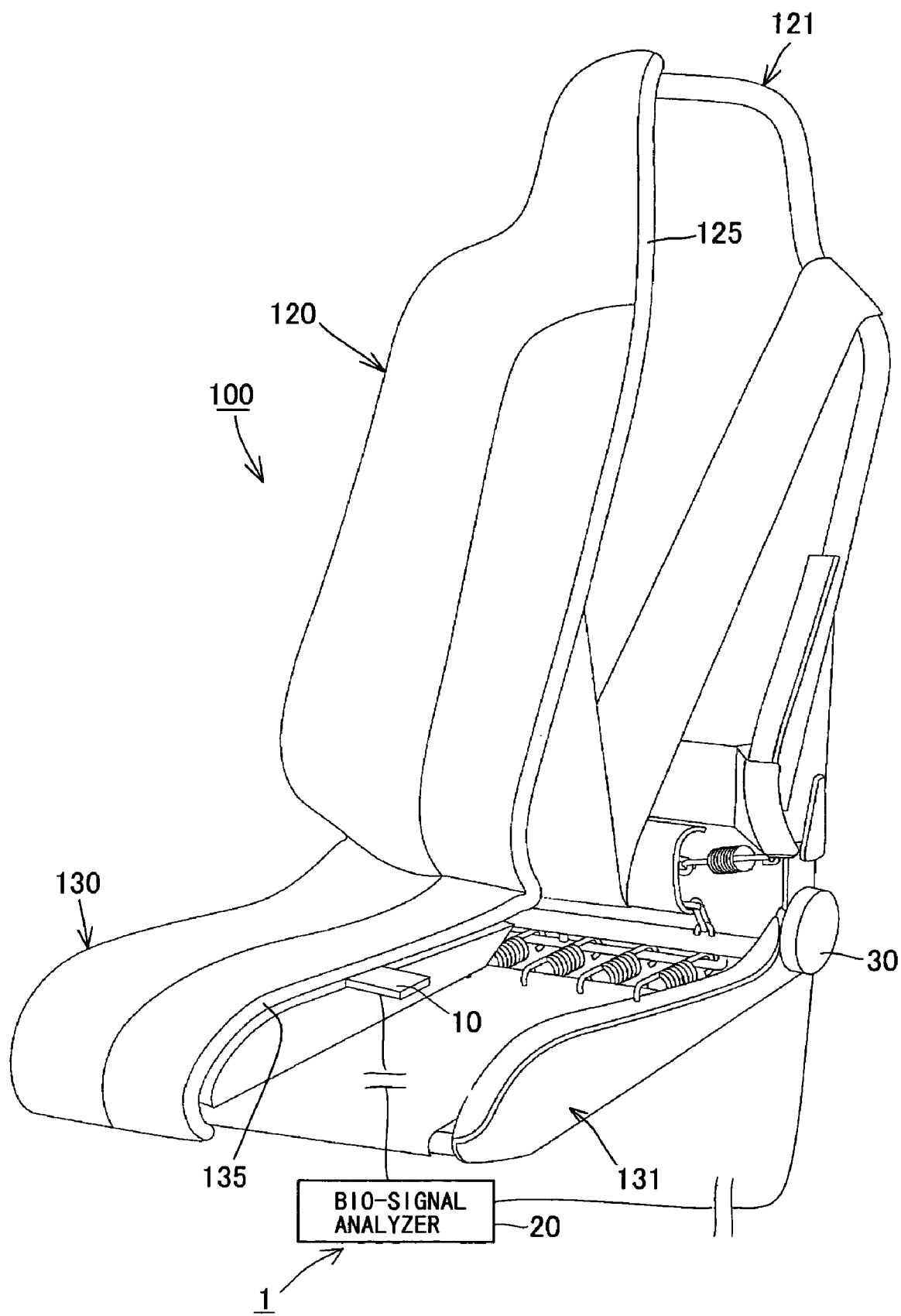
FIG. 2 is a view showing an example structure of a driver seat system according to an embodiment of the present invention.

Accordingly, the seat composed of the tension structure and provided with a bio-signal measurement instrument 10 is structurally hard to cause fatigue, beside that, the bio-signal measurement instrument 10 is able to detect a fatigue state immediately, so that the driver seat system with higher security can be provided. FIG. 2 is a view outlining a structure of such a driver seat system, in which a seat 100 is provided with the bio-signal measurement instrument 10 and an awakening device 30 and is connected with a bio-signal analyzer 20 via a signal cable. The seat 100 shown here is an example seat structure employing the cushioning layer being the tension structure. Specifically, as a seat back 120 and a seat cushion 130, solid knitted fabrics 125 and 135 are spread over a back frame 121 and a cushion frame 131, respectively.

The bio-signal analyzer 20 is composed of a Lyapunov exponent calculation means 21, a Lyapunov exponent peak value detection means 22, a bio-signal peak value detection means 23, a power value calculation means 24, a gradient calculation means 25, and a comparative determination means 26, as programs.

A Lyapunov exponent is one of chaos indicators and is a value indicating, as an indicator, a dependence degree of the chaos on the initial value, that is, an amount representing a divergence degree, in accordance with passage of time, of neighboring two trajectories among trajectories drawn by (chaos) attractors. Specifically, the bio-signal data collected by the bio-signal measurement instrument 10 is embedded by the Lyapunov exponent calculation means 21 for example at an embedded delay time of 25 msec in fourth dimension to generate an attractor. With an evolution time equaling to the embedded delay time being given, the Lyapunov exponent is calculated. For calculating the Lyapunov exponent, there are a Wolf method, a Kantz method, and the like, whereas, in the case of determining a human condition or the like of a driver, immediate calculation is important, otherwise a feedback of resultant evaluation may sometimes lose meanings. Therefore, it is preferable to use the approximate calculation of a Sano-Sawada method to practically perform a real-time processing.

The Lyapunov exponent peak value detection means 22 of the present embodiment detects a peak value for each cycle of the time-series change waveform of the Lyapunov exponent to be calculated as described above. Specifically, the peak value is detected from among original waveforms of the time-series change in the Lyapunov exponent corresponding to such an range that is identified by differentiation of the Lyapunov exponent for smoothing calculated as described above. Incidentally, as for peak values, although there are the peak value at an upper limit side and that at the lower limit side for each cycle, in this embodiment, only the peak value at the upper limit side is detected and adopted in the gradient calculation means 25 described later.

The bio-signal peak value detection means 23 detects the peak value for each cycle of the original waveform of the bio-signal data obtained by the bio-signal measurement instrument 10. Specifically, similarly to the case of detecting the peak value of the Lyapunov exponent described above, the bio-signal data is differentiated for smoothing to identify the range in the vicinity of a differential waveform gradient at zero degrees, and then the peak value is detected from among the original waveforms of the bio-signal data corresponding to the identified range.

The power value calculation means 24 divides the peak value for each cycle of original waveform of the bio-signal data obtained by the bio-signal peak value detection means 23 into those for every preset time range, for example, those for every five seconds, and a difference between an averaged upper limit side peak value and an averaged lower limit side peak value within the time range is calculated as a power value. However, for highlighting a change amount, in this embodiment, a square value of the maximum difference between the averaged peak value at the upper limit side and the averaged peak value at the lower limit side in the above-described certain time range is defined as a power value. The power value means a resistance value of the living body against intrusion and destruction from outside.

The gradient calculation means 25 calculates the gradient of each peak value of the Lyapunov exponent in a certain time range with regard to time base obtained by the Lyapunov exponent peak value detection means 22 and the gradient of the power value in a certain time range with regard to time base obtained by the power value calculation means 24 by performing slide calculation the prescribed number of times at a prescribed overlap rate with regard to the prescribed time. The slide calculation is made as described below.

For instance, for calculating a gradient for T second (s) at a slide overlap rate of 90%, first, the peak value of the Lyapunov exponent for 0 (s) to T (s) and the gradient of the power value with regard to time base is found by a least-squares method. Next, the gradient for the following time frame is calculated by the least-squares method slide calculation (1): T/10 (s)~T+T/10 (s)
slide calculation (2): 2×T/10 (s)~T+2×T/10 (s)
slide calculation (n): n×T/10 (s)~T+n×T/10 (s)

The gradient of the peak value of the Lyapunov exponent and the gradient of the power value thus obtained represent a state of energy control system and a state of energy supply system respectively, as mentioned before. Accordingly, when any of them shows a large drop in time-series change, a transition from a drowsy fatigue state through a rest state to a sleep state can be detected, the drowsy state being caused due to lowering functional status of an energy generation system, which is a functioning state of muscle, triggered by functional status of the energy control system or the energy supply system, as a cause. Beyond that, as described above, in the present embodiment, monitoring is performed not for the bio-signal data and the original waveform of the Lyapunov exponent but for respective gradients obtained by performing slide calculation which further enlarge the time-series change in functioning status of the energy control system and the energy supply system of the living body, so that delicate conditions thereof can be understood precisely.

The comparative determination means 26 is a program for comparatively determining whether the gradient of the power value shows a sudden drop or not, or for the case in which both the gradients of the power value and the Lyapunov exponent are obtained as in this embodiment, whether a state that any one of the gradient of the power value or the gradient of the Lyapunov exponent shows a sudden drop exists or not, by using the gradient of the power value and the gradient of the peak value of the Lyapunov exponent which are obtained by the gradient calculation means 25, to thereby determine the range having the sudden drop to be a predictive signal for fall-asleep for an active state to the sleep state.

The comparative determination means 26 can be structured to detect the predictive signal for fall-asleep only by the sudden drop in the gradients of the power value or the Lyapunov exponent obtained by the gradient calculation means 25, however, as can be found from an test example described later, when the gradient of the power value and the gradient of the Lyapunov exponent are shown in the same graph by overlapping with each other and when the transition from the active state to the sleep state is made, in a range just before any sudden drop or in the range of the sudden drop, the gradient of the power value and the gradient of the Lyapunov exponent are in opposite phases. Accordingly, the comparative determination means 26 can be structured to determine as the predictive signal for fall-asleep from the active state into the sleep state when the sudden drop appears together with the opposite phases.

In addition, in the test examples described below, after the sudden drop in the gradient of the power value or the gradient of the Lyapunov exponent, each time-series change in the gradient of the power value or the gradient of the Lyapunov exponent sometimes appears at a low amplitude on the whole. In this case, the subject has already entered into a sleep metabolism mode. Therefore, it is possible to additionally include a structure for determining such a waveform at a low amplitude to be a sleep state when detected by the comparative determination means 26.

Incidentally, when detecting the driver's drowsiness and outputting such signals via the output means 27 as electronic signals to actuate the awakening device 30, it is important to awaken the driver as soon as possible. Accordingly, when one of the gradients of the power value and the Lyapunov exponent shows a sudden drop, it is preferable to determine the drop to be the predictive signal for fall-asleep and output the signal to the awakening device 30 before the driver makes complete transition into the sleep state. Despite the actuation of the awakening device 30, when the above-described waveform at a low amplitude appears, the driver has already made transition into the sleep mode. Therefore, it is preferable to structure to actuate the awakening device 30 again, when the comparative determination means 26 detects the signal.

It is also possible to adopt a structure in which the seat back 120 is reclined forward or rearward when the awakening device 30 receives the electronic signal of the predictive signal for fall-asleep from the output means 27, as in the case of a reclining mechanism of the driver seat shown in FIG. 2. With the seat back 120 being reclined forward or rearward from the predetermined position, the pressure sense (the sensation of pressure) is stimulated since shearing force and force giving normal force (shift force) are generated with regard to the muscles. For stimulating the pressure sense effectively, preferably, the seat back 120 set at a normal driving position of the driver is structured to recline forward. If the seat back 120 is reclined to a large degree, the driver may have a trouble with driving operation, whereby, it is preferable to make the angle to recline be as small as possible. According to an experiment by the present inventor, it is found that the seat back 120 reclined at an angle of 20 minutes to 5 degrees to the angle before reclining is enough to stimulate the pressure sense to thereby recover the wakeful state or awakening state, and that this angle range makes no trouble in driving and thereby be preferable as an angle to recline. That is, if the seat is reclined at an angle of below 20 minutes, it is difficult to sense it, and if the seat is reclined at an angle of over 5 degrees, the driver may have trouble driving.

The awakening device 30 starts operation in response to the electronic signal of the predictive signal for fall-asleep outputted from the output means 27 of the bio-signal analyzer 20, and causes the shift force as described before to thereby stimulate the pressure sense of the driver. With the structure stimulating the pressure sense, it is possible to awaken the driver more surely, without regard to an alarm reaction level to an alarm sound. It should be noted that the other means which stimulate an acoustic sense (a sense of hearing) or a visual sense (a sense of sight) of the human can be used concurrently, in addition to the wakefulness recovery device 30 for stimulating the pressure sense.

As a means for stimulating the acoustic sense, for example, an alarm sound generation device such as a buzzer which generates an alarm sound can be used. As a means for stimulating the visual sense, a warning light can be used by building the warning light in any portion of vehicle components positioning forward of the seated position of the driver such as in an instrument panel or a display for a navigation system, and by structuring to light-on or blink the warning light when received the electronic signal of the predictive signal for fall-asleep from the output means 27.

Further, in the monitor 1, preferably, there is provided an guide route search and display device 40 for searching a nearest parking area based on current location of the vehicle to display a guidance route to the parking area on a display of a vehicle navigation system when received the predictive signal for fall-asleep, the guide route search and display device 40 being provided to be able to receive an output signal from the output means 27 of the bio-signal analyzer 20. The guide route search and display device 40 is composed of a program and is realizable by being set in the vehicle navigation system. Incidentally, the display mentioned here is not limited to the built-in display of the normal vehicle navigation system as long as it is a means for displaying information by interlocking with the geographical information and the positional information of the vehicle navigation system, and such as the display built in the installment panel and the display for displaying on a windshield are also acceptable.

Furthermore, a communication means 28 is preferably provided so that the communication means 28 is capable of receiving an output signal from the output means 27 of the bio-signal analyzer 20. It is thereby possible to communicate the predictive signal for fall-asleep to a control center for controlling vehicles by the communication means 28. As a communication means 28, a communication terminal such as a cellular phone, a personal handy-phone system, and the like can be used as long as they can communicate with the control center via an Internet, a public telephone line, and the like. The control center is able to alert the driver appropriately by wireless communications and the like since the control center is enabled to know the driver feeling drowsiness with certainty.

TEST EXAMPLE

Subsequently, a sleep test is conducted for four subjects who are seated on the seats, in which time-series changes in the gradient of the power value (Power gradient) and in the peak value of the gradient of the Lyapunov exponent (Lyapunov exponent gradient) are obtained. The seat used in this test is that shown in FIG. 2, which is provided with the cushioning layer composed of the tension structure being the solid knitted fabrics 125 and 135 spread over the back frame 121 and the cushion frame 135 respectively at a stretch rate of below 5%. By mounting a pressure sensor, as a bio-signal measurement instrument 10, on the reverse surface of the solid knitted fabric 135 under a haunch portion, the measurement is conducted. The pressure sensor used in this test is a film-shaped piezoelectric element (product name: PIEZO FILM LDT series LDT4-028K/L, by Tokyo Sensor Co. Ltd.). The calculations of the Power gradient and the Lyapunov exponent gradient are made after obtaining the peak values of the collected bio-signal data and the Lyapunov exponent for every 5 seconds over the whole measurement time. In the gradient calculating means, the slide overlap rate is set at 90%, and a first gradient calculation is made for first three minutes after starting measurement. That is, firstly, respective gradients are calculated for a time range of 0 to 180 seconds after starting measurement, secondly, respective gradients are calculated for the time range of 18 to 198 seconds after starting measurement, thirdly, respective gradients are calculated for the time range of 36 to 216 seconds after starting measurement, and, for the calculation, this procedure is repeated until the measurement time comes to an end. The calculation results are plotted with regard to the time measured, respectively.

Test Example 1

Subject: A (sex: male, age: 62, height: 160 cm, weight: 62 kg, health condition: has a touch of autonomic imbalance) The measurement is conducted by seating the subject on the seat in a comfortable position for 24 minutes.

Figure 3:
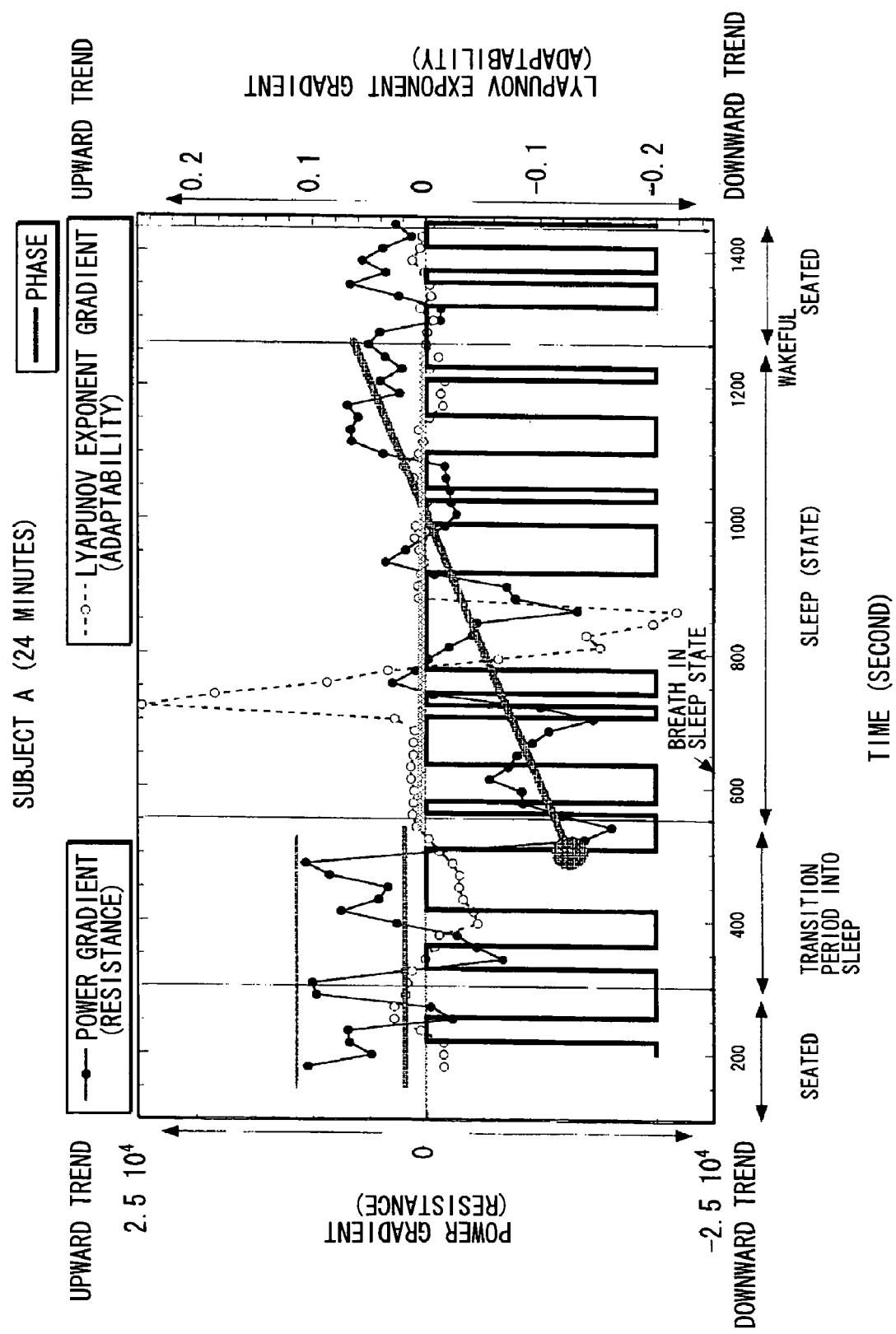
FIG. 3 is a graphical chart showing gradients of a power value and a Lyapunov exponent in test example 1.

Result:
FIG. 3 shows a Power gradient and a Lyapunov exponent gradient of test example 1.

(1) Remarks by an Observer

The subject enters into a rest state after 300 seconds, starts breathing in a sleep state after 600 seconds, and awakes after 1250 seconds.

(2) Considerations

As shown in FIG. 3, the Power gradient shows a large drop around 300 to 330 seconds and a larger drop around 550 to 600 seconds, and thereafter, the Power gradient shows upward trend and at the same time the amplitude of the Lyapunov exponent gradient becomes smaller. This is considered to be an increase in a defensive physical capability to maintain life and health as a result of a transition into the sleep state. The Power gradient drops around 300 to 330 seconds and around 550 to 600 seconds therebefore are considered to be a period changing from an active state into the sleep state (rest metabolism to sleep metabolism). That is, in this period, the subject is considered to be in a transition period into sleep with a feeling of drowsiness.

As is also shown in the remarks by the viewer, the subject starts breathing in a sleeping state after 600 seconds, which supports the determination of the human condition made in view of the Power gradient trend. Based on this, it is found that to know the Power gradient trend allows knowing a state of energy metabolism of the living body. Therefore, when the Power gradient shows a large drop in the comparative determination means 26 of the bio-signal analyzer 20, by outputting a detected signal of the drop as an electronic signal to the awakening device 30 via the output means 27 to thereby actuate the awakening device 30, it is possible to awaken the driver. Further, when provided with the guide route search and display device 40, it is possible to induce the driver to take a rest at a nearest parking area.

Test Example 2

Subject: B (sex: male, age: 47, height: 168 cm, weight: 67 kg, health condition: fine) The measurement is conducted by seating the subject on the seat in a comfortable position for 24 minutes.

Figure 4:
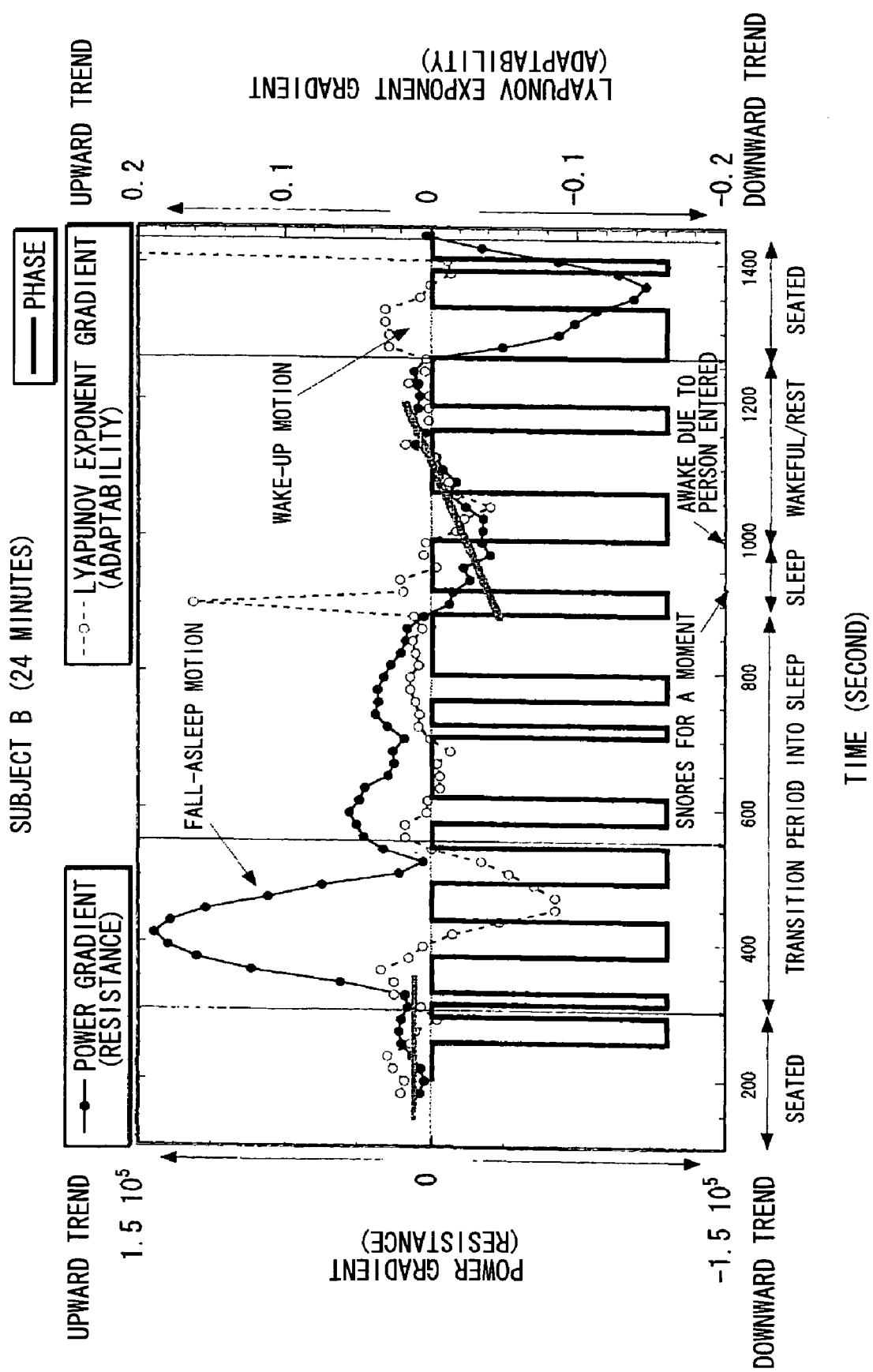
FIG. 4 is a graphical chart showing the gradients of the power value and the Lyapunov exponent in test example 2.

Result:
FIG. 4 shows a Power gradient and a Lyapunov exponent gradient of test example 2.

(1) Remarks by an Observer

The subject shows a motion falling asleep (fall-asleep motion) after 400 seconds, and snores for a moment around 920 seconds, but seems to awake around 1000 seconds since someone enters into the testing site. The subject shows an wake-up motion after 1300 seconds.

(2) Considerations

As shown in FIG. 4, when the subject shows the fall-asleep motion around 400 to 500 seconds, the Power gradient largely drops and the Lyapunov exponent gradient also drops. This indicates that the subject gradually makes transition from the wakeful state or awakening state into the rest state. The Power gradient falls to negative area thereafter around 600 to 900 seconds. After that, when the Power gradient shows a slight upward trend, someone enters into the test site, so that the subject stays in a kind of a border between the wakeful state or awakening state and the rest state, in which the slight upward trend can be considered to be an increase in the defensive physical capability for maintaining life and health, so that the transition from the active state into the sleep state (rest metabolism to sleep metabolism) is considered to be made in the range from the first large drop of the Power gradient to near the drop around 600 to 900 seconds.

The human condition considered from viewpoints of the Power gradient and the Lyapunov exponent gradient in FIG. 4 essentially agrees with the remarks by the observer described above. Based on this, it is found that focusing attention on the Power gradient and the Lyapunov exponent gradient allows knowing the human condition. Therefore, by outputting a detected signal, which is detected in the comparative determination means 26 of the bio-signal analyzer 20 when the Power gradient shows the large drop, to the awakening device 30 via the output means 27, as an electronic signal, the awakening device 30 is actuated, so that the driver can revert to the wakeful state or awakening state.

Test Example 3

Subject: C (sex: female, age: 25, height: 167 cm, weight: 63 kg, health condition: fine) The measurement is conducted by seating the subject on the seat in a comfortable position for 65 minutes.

Figure 5:
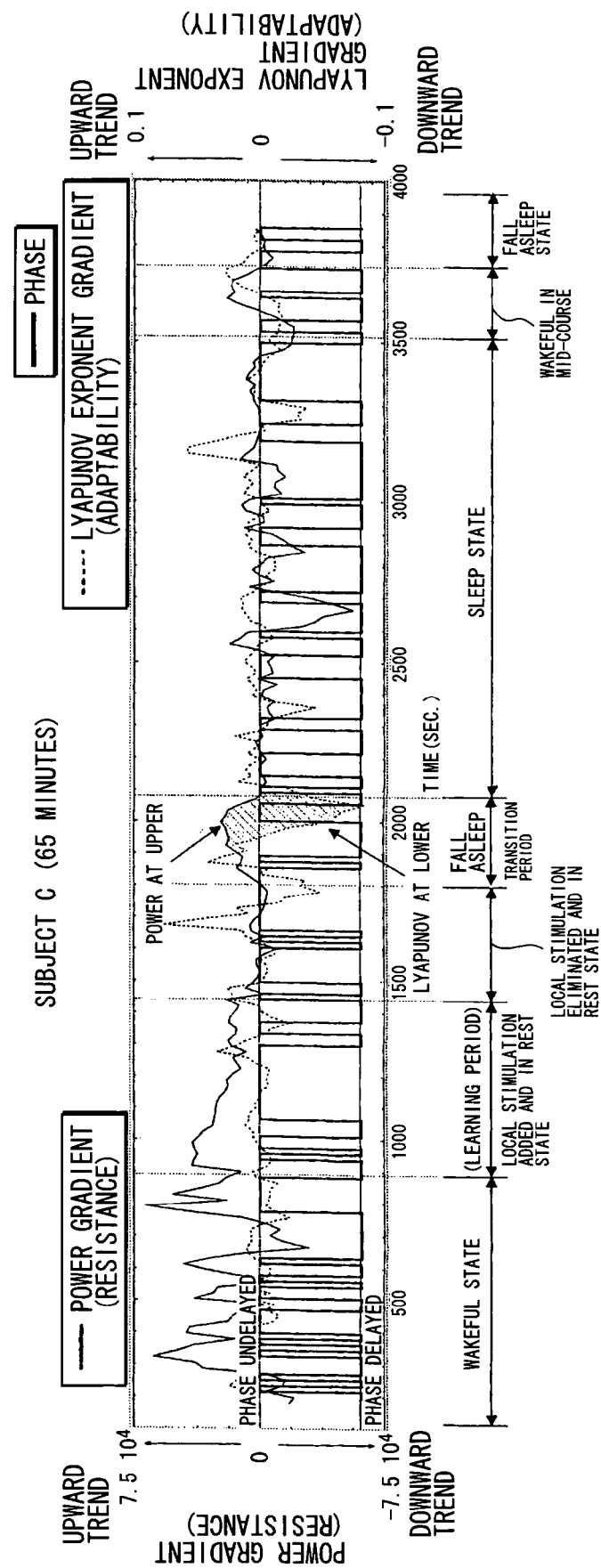
FIG. 5 is a graphical chart showing the gradients of the power value and the Lyapunov exponent in test example 3.

Result:
FIG. 5 shows a Power gradient and a Lyapunov exponent gradient of test example 3.

(1) Remarks by an Observer

The subject seems to be the rest state after 900 seconds and fall asleep after 2000 seconds.

(2) Considerations

As shown in FIG. 5, the amplitude of the Power gradient becomes small after 900 seconds and the amplitude becomes further small after 1400 seconds. This indicates that the subject makes the transition from the wakeful state into the rest state, and whereby the living body enters into a stable state. Yet, thereafter, the Power gradient shows an upward trend after around 1800 seconds while the Lyapunov exponent gradient largely drops until around 2000 seconds. Thereafter, both the Power gradient and Lyapunov exponent gradient move at a low amplitude. This can be considered due to the energy metabolism change into the sleep metabolism mode, whereby the adjacent large drop in the Lyapunov exponent gradient is considered to be a stage making transition into a sleep helped by highly achieved psychological stability. Also, in the remarks by the observer, the subject seems to fall asleep after 2000 seconds. Therefore, the range in which the Lyapunov exponent gradient shows the drop can be determined to be the transition period into sleep.

Consequently, in the case of the subject C, it can be said that the drop in the Lyapunov exponent gradient appears more apparently than the drop in the Power gradient. Therefore, the present invention is preferably structured so that the detection of the Lyapunov exponent gradient is performed in addition to the detection of the Power gradient, and a timing in which any one of the drops appears is determined to be the predictive signal for fall-asleep by the comparative determination means 26. The structure allows the actuation of the awakening device 30 in more appropriate manner, without regard to individual differences.

Figure 6:
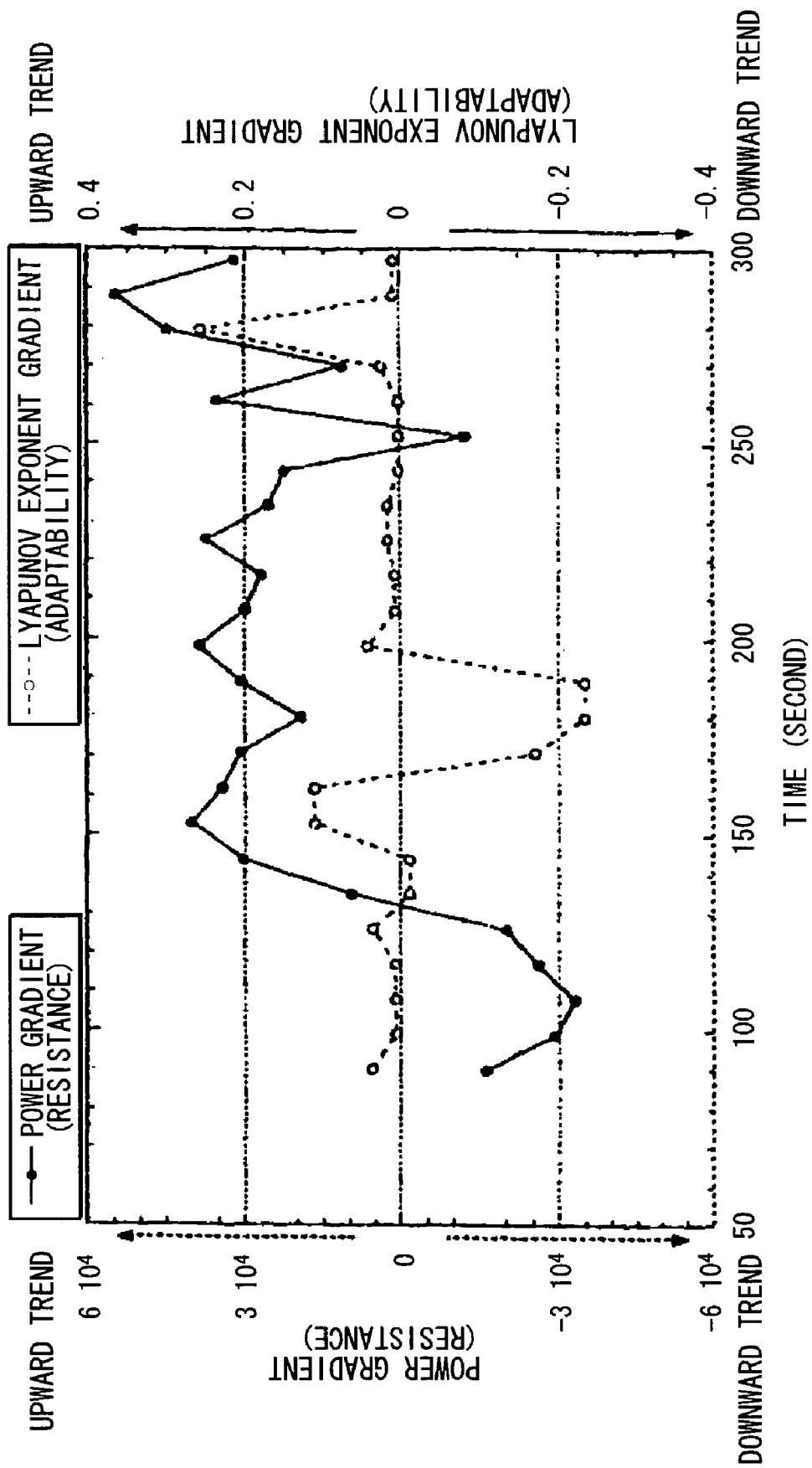
FIG. 6 is a graphical chart showing the gradients of the power value and the Lyapunov exponent by causing a shift force against the subject in test example 3 by reclining a seat back in a transition period into sleep.

Subsequently, the sleep test is conducted again to the same subject C under the same conditions, but this time, the seat back is reclined forward at an angle of approximately 2 degrees by the reclining mechanism when the Lyapunov exponent gradient shows a large drop. FIG. 6 shows the Lyapunov exponent gradient and the Power gradient after reclining the seat back. As shown in FIG. 6, in the range from just after reclining the seat back (at 90 seconds in FIG. 6 because of the slide calculation) to 150 seconds, both the Power gradient and Lyapunov exponent gradients go up, it is whereby understood that the subject responds to an external stimulus and is in the course of the transition into the wakeful state or awakening state. After 150 seconds, the Lyapunov exponent gradient once drops but goes up again, in which the drop indicates the response to the external stimulus, so that the subject is completely in the wakeful state or awakening state at this point. Therefore, it is found that a stimulation of a pressure sense by reclining the reclining mechanism and thereby causing a shift force allows to recover a person the wakeful state or awakening state most surely. Alternatively, it can be structured so that the wakeful state or awakening state is kept by reclining the seat back repeatedly for a certain time range, at random, periodically, or in a pulsed manner (for instance, with periodicity in accordance with human respirations). For instance, it is possible to structure to recline and vibrate the seat back for a certain time range while the driver is guided to the nearest parking area by the guide route search and display device 40.

As a consequence of all the test results above, here, they have the following in common: after a sudden drop of the Power gradient or the Lyapunov exponent gradient, at least one of the Power gradient or the Lyapunov exponent gradient moves at a low amplitude, the Power gradient and the Lyapunov exponent gradient are in opposite phases in a sudden drop range or just before the sudden drop range, which indicates a resistance against the transition into the sleep state (around 400 to 500 seconds in FIG. 3, around 200 to 500 seconds in FIG. 4, and around 1900 to 2100 seconds in FIG. 5). Accordingly, by determining the range, which has the sudden drop in the Power gradient or the Lyapunov exponent gradient while they are in the opposite phases, to be the predictive signal for fall-asleep, it is possible to detect the state just before falling asleep more surely.

Test Example 4

Subject: D (sex: male, age: 25, height: 175 cm, weight: 65 kg, health condition: fine) The measurement is conducted by seating the subject on the seat in a comfortable position for 30 minutes.

Figure 7:
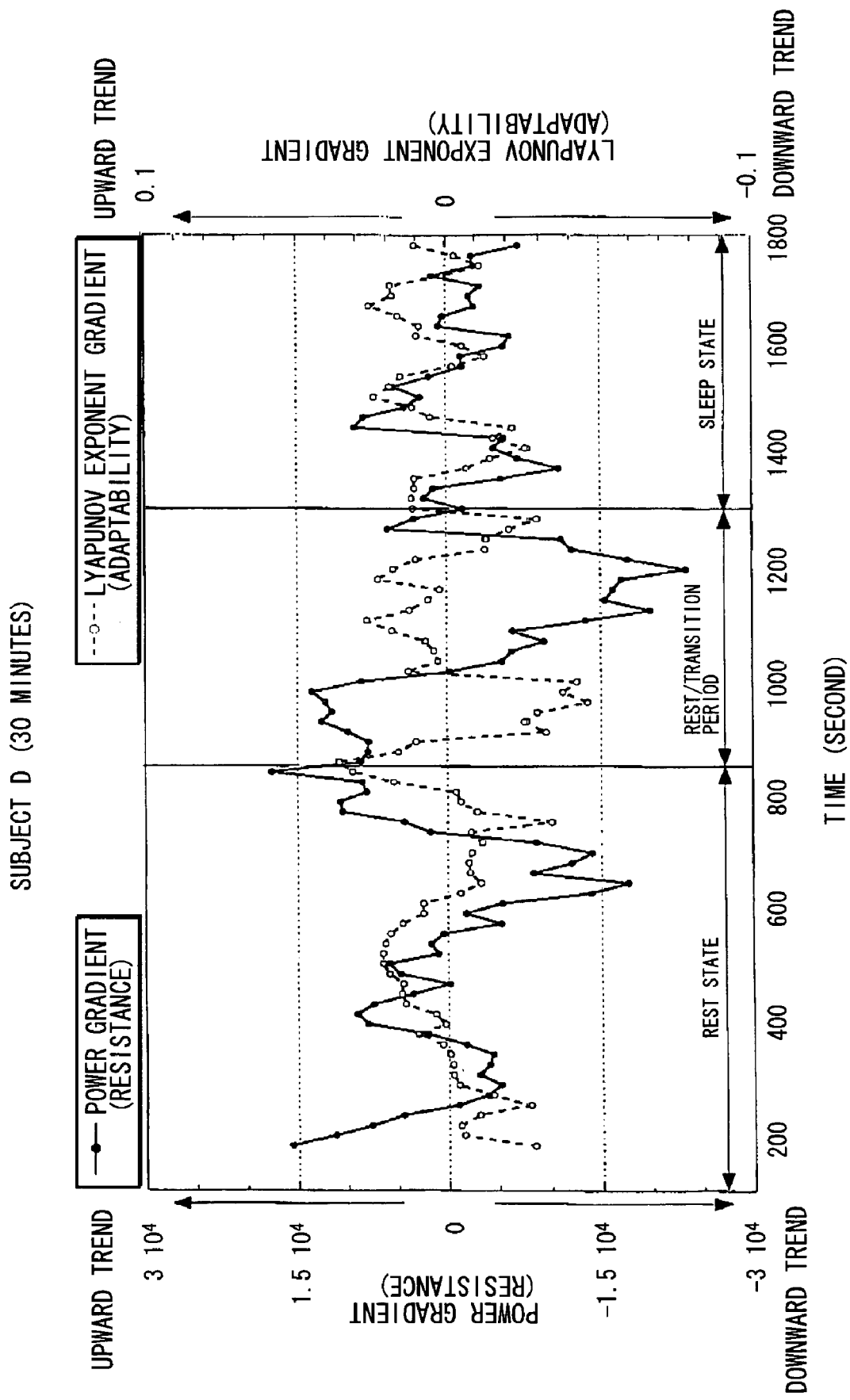
FIG. 7 is a graphical chart showing the gradients of the power value and the Lyapunov exponent in test example 4.

Result:

FIG. 7 shows a Power gradient and a Lyapunov exponent gradient of test example 4.

(1) Remarks by an Observer

The subject seems to start dozing after 800 seconds and be in complete sleep around 1400 seconds.

(2) Considerations

As shown in FIG. 7, both the Power gradient and Lyapunov exponent gradient move in substantially same phase until around 850 seconds, from which it is found that the energy metabolism is becoming stable. Thereafter, the Lyapunov exponent gradient drops largely around 850 to 1000 seconds while the Power gradient goes up, where they are in the opposite phases. In around 1000 to 1200 seconds, the Power gradient drops largely while the Lyapunov exponent gradient goes up, where they are in the opposite phases. After 1300 seconds, both the Lyapunov exponent gradient and Power gradient move in a low amplitude to converge.

Accordingly, at the time of the first large drop in the Lyapunov exponent gradient, the subject is psychologically stable but still consumes high calories, which can deemed to be a preparative stage for the transition period into sleep. At the time of the following large drop in the Power gradient, the subject consumes lower calories, which is a latter part of the transition period into sleep. At the time when the gradients are in the low amplitude thereafter, both the Power gradient and the Lyapunov exponent gradient are higher as compared to those in the transition period into sleep but are still in a low amplitude, therefore, it is considered to be the sleep state in which the defensive physical capability functions to maintain life and health.

Specifically, in the case of the subject D, after the appearance of the sudden drop in the Power gradient or the Lyapunov exponent gradient mentioned above, at least one of the Power gradient or the Lyapunov exponent gradient moves in a low amplitude, and in the sudden drop range or just before the sudden drop range, the sudden drop in the Power gradient or the Lyapunov exponent gradient appears while they are in the opposite phases, as a typical trend.

Figure 9:
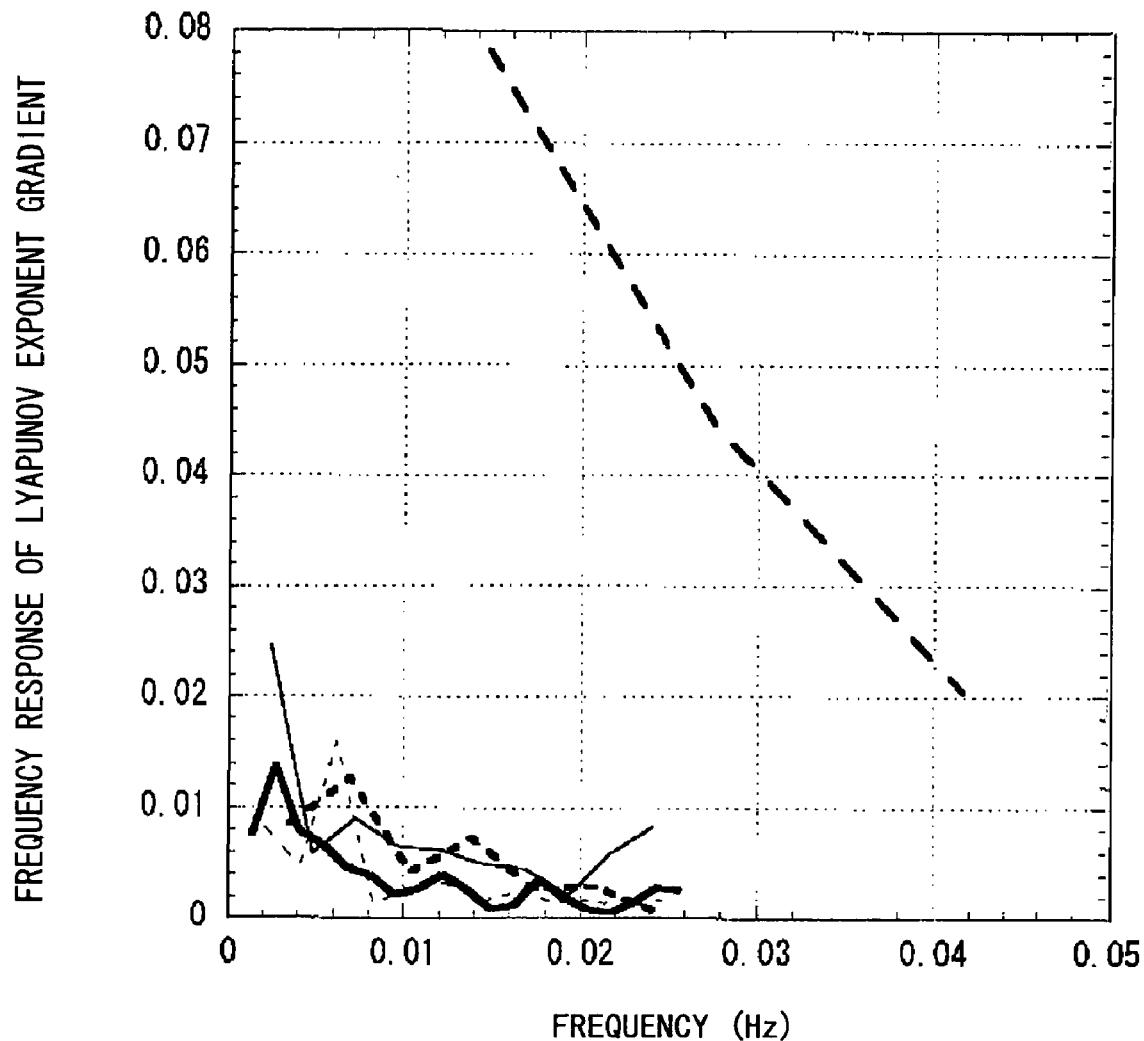
FIG. 9 is a graphical chart showing a result of the frequency analysis on the gradient of the Lyapunov exponent in test example 4.

In addition, in an attempt to validate further, a frequency analysis is performed on the data in FIG. 7. FIG. 8 shows a result of the frequency analysis on the Power gradient, and FIG. 9 shows a result of the frequency analysis on the Lyapunov exponent gradient. As is clearly shown in FIG. 8 and FIG. 9, the frequency response in the transition period into sleep has a protruding frequency zone, as compared to those in the rest state and the sleep state, proving a large difference.

Figure 11:
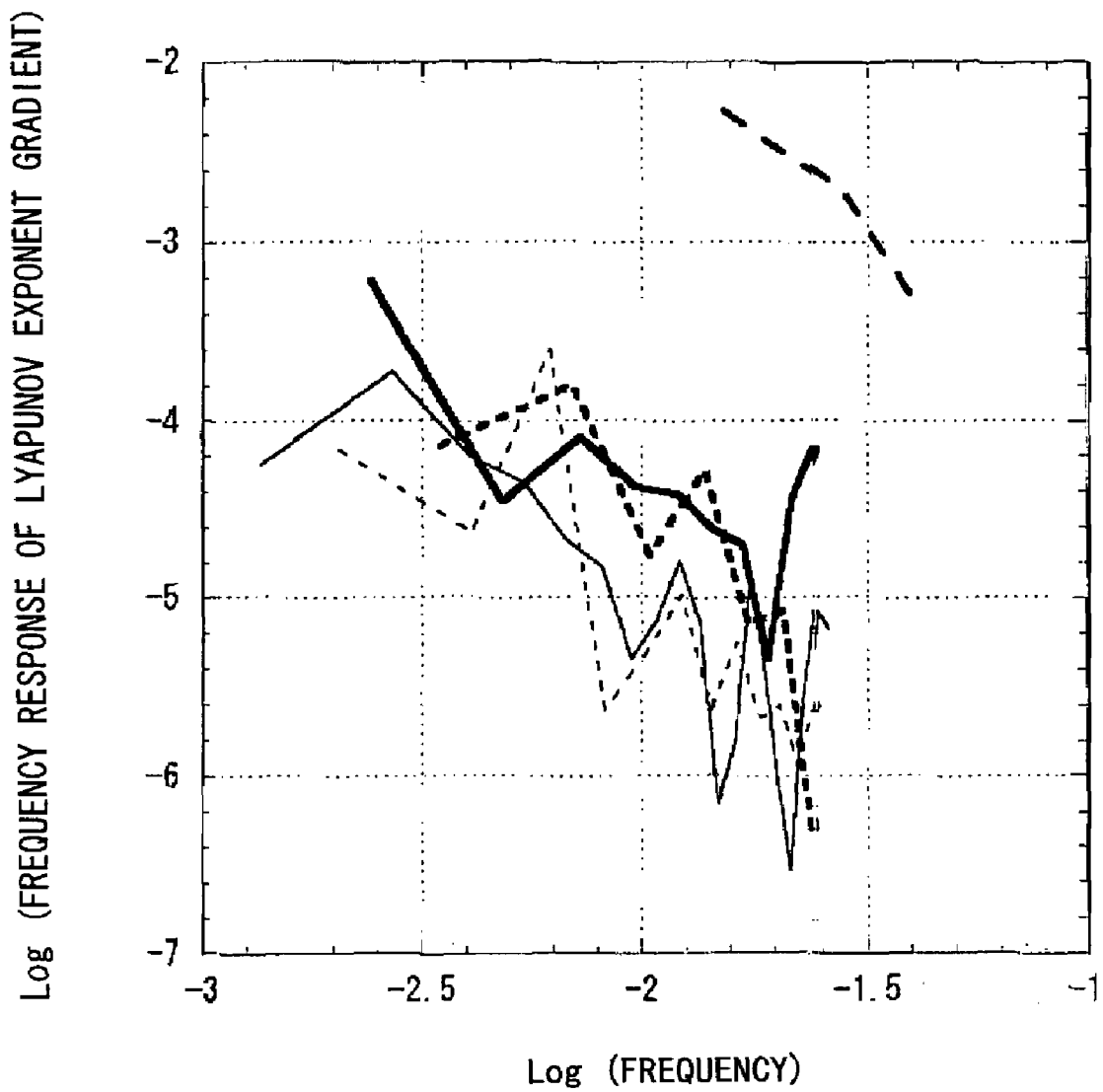
FIG. 11 is a graphical chart plotting the relation between frequency response of the gradient of the Lyapunov exponent and frequency with regard to the logarithm axis from the frequency analysis in FIG. 9.

FIG. 10 is a view plotting the relation between the frequency response of the Power gradient and the frequency with regard to the logarithm axis based on the frequency analysis result in FIG. 8; and FIG. 11 is a view plotting the relation between the frequency response of the Lyapunov exponent gradient and the frequency with regard to the logarithm axis from the frequency analysis in FIG. 9. As shown in these drawings, a gradient β in the transition period into sleep is smaller than that in the sleep state. Although the gradient β temporarily goes higher than that in the transition period just after entering into the sleep state, this can be considered as an increase in the defensive physical capability for maintaining life and health in the sleep state, and the smaller gradient β therebefore can be considered to be the transition period into sleep. As for the Lyapunov exponent gradient, the gradient β in the transition period into sleep is smaller than both of those in the rest state and the sleep state, indicating very well that the subject is making transition into the sleep state in the transition period into sleep under the condition psychologically relaxed.

Based on this, it is understood that more correct determination of the transition period into sleep can be attained by adopting this frequency analysis when determining the transition period into sleep. Therefore, the bio-signal analyzer used in the present invention can also be structured to additionally include a frequency analysis means. However, the frequency analysis is to be performed after the calculation of the Power gradient and the Lyapunov exponent gradient, therefore, generally, the alarm timing is to be delayed since the actuation of the awakening device 30 is made after receiving the result of the frequency analysis. Nevertheless, there are some programs which can perform, as an example, the frequency analysis substantially in parallel with the calculation by the gradient calculation means 25, which realizes immediate output, whereby it is possible to structure so that the awakening device 30 is actuated in response to the determination based also on the frequency analysis result. Further, the determination of the transition period into sleep such as a drop or the like in the Power gradient and/or the Lyapunov exponent gradient can also be made by recording a sleep pattern of the driver in advance and by comparing the sleep pattern with the Power gradient and/or the Lyapunov exponent gradient.

In addition, the sleep test is conducted again to the same subject D in test example 4 under the same conditions, but this time, the seat back is reclined forward at an angle of approximately 3 degrees just after the transition period into sleep in which the Power gradient drops largely. FIG. 8 and FIG. 9 show the results of the frequency analyses on the Power gradient and the Lyapunov exponent gradient at that time, and FIG. 10 and FIG. 11 are views plotting the relations between the frequency response of the Power gradient and frequency, and the frequency response of Lyapunov exponent gradient and frequency obtained from the frequency analyses results, respectively, with regard to the logarithm axis. Also, the frequency analysis result and frequency response of the subject in the active state before entering into the rest state are similarly shown therein.

As a result, as shown in FIGS. 8 to 11, it is found that when applying a shift force by reclining the seat back, both the Power gradient and Lyapunov exponent gradient show greatly exceeding values as compared with those in the normal active state, indicating the recovery of the wakeful state or awakening state at an extreme high level with energy amount being highly increased.

A driver seat system and an awakening device of the present invention is structured to start operation in response to a predictive signal for fall-asleep received from a monitor to thereby stimulate a pressure sense of a driver. Therefore, without regard to an alarm reaction level to an alarm sound, it is possible to stimulate the driver, so that the driver can recover the wakeful state or awakening state more surely. Particularly, with the use of a reclining mechanism which stimulates the pressure sense by reclining the seat back and whereby causing a shift force, it is possible to stimulate the pressure sense more surely even with more simple structure.

Additionally, the driver seat system according to the present invention includes, in its bio-signal analyzer composing a monitor, a bio-signal peak value detection means for detecting a peak value for each cycle of an original waveform of the bio-signal data, a power value calculation means for calculating a difference between the peak value at an upper limit side and the peak value at a lower limit side for each certain time range using respective peak values obtained by said bio-signal peak value detection means to thereby set the difference as a power value, so that a determination of the predictive signal for fall-asleep for energy metabolism transition from an active state to a sleep state can be made based on a time-series change in the power value. Therefore, according to the present invention, it is possible to perform a novel evaluation of human condition focusing on a functioning state of an energy supply system of a living body, differently from the conventional evaluation of human condition using the Lyapunov exponent as an indicator, which makes is possible to determine the predictive signal for fall-asleep from the active state to the sleep state even in the case where the determination is difficult only with the Lyapunov exponent as an indicator, so that the present invention is suitable for preventing the fall asleep at the wheel.

Further, by adopting a means concurrently using the Lyapunov exponent of the bio-signal in addition to the power value, as a bio-signal analyzer, it is possible to determine the human condition more accurately without regard to individual differences and health conditions, allowing the prevention of the fall asleep at the wheel, more surely.

Moreover, the present invention further includes a gradient calculation means for obtaining gradient(s) of the power value and/or the Lyapunov exponent with regard to time base in a certain time range by performing slide calculation the prescribed number of times at a prescribed overlap rate with regard to the prescribed time, allowing correct and real-time determination of the time-series change(s) in the power value and/or the Lyapunov exponent, so that the transition from the active state into the sleep state can be detected more accurately.

What is claimed is:

1. A driver seat system comprising:
    a monitor for monitoring a human condition of a driver, and
    an awakening device for making the driver recover a wakeful state or awakening state by starting operation when received a predictive signal for fall-asleep from said monitor, the predictive signal for fall-asleep being a signal when an energy metabolism makes transition from an active state into a sleep state,
    wherein said awakening device includes a mechanism for stimulating a pressure sense of the driver and wherein said monitor includes a bio-signal measurement instrument for measuring a bio-signal of the driver, and a bio-signal analyzer for analyzing a bio-signal data collected by said bio-signal measurement instrument, said bio-signal analyzer including:
        a bio-signal peak value detection means for detecting a peak value for each cycle of an original waveform of the bio-signal data;
        a power value calculation means for calculating a difference between the peak value at an upper limit side and the peak value at a lower limit side for each certain time range using respective peak values obtained by said bio-signal peak value detection means to thereby set the difference as a power value;
        a gradient calculation means for obtaining a gradient of the power value with regard to time base in a certain time range by performing slide calculation the prescribed number of times at a prescribed overlap rate with regard to the prescribed time;

a comparative determination means for comparatively determining whether a sudden drop state of the gradient of the power value exists or not in time-series change in the gradient of the power value obtained by performing slide calculation with said gradient calculation means to thereby determine a time range in which the sudden drop state appears to be the predictive signal for fall-asleep from the active state into the sleep state; and an output means for outputting the predictive signal for fall-asleep from the active state to the sleep state detected by said comparative determination means.

2. The driver seat system according to claim 1, wherein said awakening device for stimulating the pressure sense is a reclining mechanism for reclining a seat back of a driver seat forward or rearward to thereby stimulate the pressure sense of the driver by causing a shift force.

3. The driver seat system according to claim 2, wherein an angle of the seat back of the driver seat to recline is set at an angle of 20 minutes to 5 degrees as compared to the state before changing the reclining angle of the seat back for stimulating the pressure sense.

4. The driver seat system according to claim 1, wherein said bio-signal analyzer further includes a Lyapunov exponent calculation means for calculating a Lyapunov exponent by performing chaos theory analysis on the bio-signal data, and a Lyapunov exponent peak value detection means for detecting a peak value for each cycle of a time-series change waveform of the Lyapunov exponent calculated by said Lyapunov exponent calculation means, wherein said gradient calculation means includes a means for obtaining, in addition to the gradient of the power value, a gradient of respective peak values of the Lyapunov exponent with regard to time base in a certain time range obtained by said Lyapunov exponent peak value detection means, and wherein said comparative determination means comparatively determines whether the sudden drop state exists or not in at least one of the time-series changes in the gradients of the power value and the Lyapunov exponent obtained by performing slide calculation with said gradient calculation means to determine a range in which the sudden drop state appears to be the predictive signal for fall-asleep from the active state into the sleep state.

5. The driver seat system according to claim 4, wherein said comparative determination means compares the time-series changes in the gradients of the power value and the Lyapunov exponent which are obtained by performing slide calculation with said gradient calculation means, and determines whether the gradient of the power value and the gradient of the Lyapunov exponent are in opposite phases with each other before or in the range the sudden drop appears in the gradient of the power value or in the gradient of the Lyapunov exponent, and in the case where the sudden drop in the gradient of the power value or in the gradient of the Lyapunov exponent appears while they are in the opposite phases, said comparative determination means determines the range to be the predictive signal for fall-asleep from the active state into the sleep state.

6. The driver seat system according to claim 4, wherein said comparative determination means includes a means for determining that the transition into the sleep state is made when the time-series change in the gradient of the power value or in the gradient the Lyapunov exponent appears at a low amplitude on the whole after the sudden drop appears in the gradient of the power value or in the gradient of the Lyapunov exponent, respectively.

7. The driver seat system according to claim 1, wherein said bio-signal peak value detection means includes a means for carrying out differentiation of the bio-signal data for smoothing to identify a range in the vicinity of a differential waveform gradient at zero degrees to thereby detect the peak value from the original waveform corresponding to the range identified.

8. The driver seat system according to claim 4, wherein said Lyapunov exponent peak value detection means includes a means for carrying out differentiation of the Lyapunov exponent for smoothing to identify a range in the vicinity of a differential waveform gradient at zero degrees to thereby detect the peak value from the original waveform corresponding to the range identified.

9. The driver seat system according to claim 1, wherein said power value calculation means is a means for calculating, as a power value, a difference between an average peak value at the upper limit side and an average peak value at the lower limit side both in a certain time range of the bio-signal data.

10. The driver seat system according to claim 4, wherein the gradient of the power value or the gradient of the Lyapunov exponent calculated by said gradient calculation means is a value obtained by a least-squares method.

11. The driver seat system according to claim 1, wherein said bio-signal measurement instrument is a pressure sensor to be mounted in at least one of a seat cushion and the seat back of the driver seat.

12. The driver seat system according to claim 11, wherein a cushioning layer composing the seat cushion and the seat back is a tension structure causing a difference in tension depending on presence or absence of a person seated on the driver seat, and wherein the pressure sensor is mounted in the cushioning layer being the tension structure.

13. The driver seat system according to claim 1, further comprising a guide route search and display device for searching a guide route to a nearest parking area based on current location of a vehicle to display the guide route on a display of a vehicle navigation system when received the predictive signal for fall-asleep, the guide route search and display device being provided to be able to receive a signal from said monitor.

14. The driver seat system according to claim 1, further comprising a communication means capable of communicating the predictive signal for fall-asleep to a control center which controls vehicles, the communication means being provided to be able to receive a signal from said monitor.

15. An awakening device which starts operation when received a predictive signal for fall-asleep for energy metabolism transition from an active state into a sleep state from a monitor for monitoring a human condition of a driver, comprising a mechanism for stimulating a pressure sense of the driver to awaken the driver, wherein said monitor includes a bio-signal measurement instrument for measuring a bio-signal of the driver, and a bio-signal analyzer for analyzing a bio-signal data collected by said bio-signal measurement instrument, said bio-signal analyzer including:

a bio-signal peak value detection means for detecting a peak value for each cycle of an original waveform of the bio-signal data;

a power value calculation means for calculating a difference between the peak value at an upper limit side and the peak value at a lower limit side for each certain time range using respective peak values obtained by said bio-signal peak value detection means to thereby set the difference as a power value;

a gradient calculation means for obtaining a gradient of the power value with regard to time base in a certain time range by performing slide calculation the prescribed number of times at a prescribed overlap rate with regard to the prescribed time;

a comparative determination means for comparatively determining whether a sudden drop state of the gradient of the power value exists or not in time-series change in the gradient of the power value obtained by performing slide calculation with said gradient calculation means to thereby determine a time range in which the sudden drop state appears to be the predictive signal for fall-asleep from the active state into the sleep state; and an output means for outputting the predictive signal for fall-asleep from the active state to the sleep state detected by said comparative determination means.

16. The awakening device according to claim 15, wherein said mechanism for stimulating the pressure sense is a reclining mechanism which simulates the pressure sense of the driver by causing a shift force by reclining a seat back of a driver seat forward or rearward.

17. The awakening device according to claim 16, wherein an angle of the seat back of the driver seat to recline is set at an angle of 20 minutes to 5 degrees as compared to the state before changing the reclining angle of the seat back for stimulating the pressure sense.

* * * * *